United States Patent
Alexandre

(10) Patent No.: US 6,697,516 B1
(45) Date of Patent: Feb. 24, 2004

(54) METHOD FOR INSPECTING THE SURFACE OF A MOVING STRIP BY PRIOR CLASSIFICATION OF THE DETECTED SURFACE IRREGULARITY

(75) Inventor: Patrick Alexandre, Gray (FR)

(73) Assignee: Sollac, Puteaux (FR)

( * ) Notice: Subject to any disclaimer, the term of this patent is extended or adjusted under 35 U.S.C. 154(b) by 0 days.

(21) Appl. No.: 09/381,954

(22) PCT Filed: Mar. 25, 1998

(86) PCT No.: PCT/FR98/00603

§ 371 (c)(1),
(2), (4) Date: Nov. 1, 1999

(87) PCT Pub. No.: WO98/44337

PCT Pub. Date: Oct. 8, 1998

(30) Foreign Application Priority Data

Mar. 28, 1997 (FR) ............................................. 97 03897

(51) Int. Cl.[7] ................................................. G06K 9/00
(52) U.S. Cl. ...................... 382/149; 356/237.1; 438/14; 438/16
(58) Field of Search ............................... 382/147, 149, 382/145, 141; 356/237.1, 14, 16

(56) References Cited

U.S. PATENT DOCUMENTS 4,519,041 A * 5/1985 Fant et al. .................. 382/108
5,991,699 A * 11/1999 Kulkarni et al. .............. 438/10

OTHER PUBLICATIONS

Brzakovic et al. "Designing a Defect Classification System: A Case Study." Dec. 5, 1995. Pattern Recognition Society. Pattern Recognition. vol. 29, No. 8, pp. 1401–1419.*

* cited by examiner

Primary Examiner—Jayanti K. Patel
Assistant Examiner—Aaron Carter
(74) Attorney, Agent, or Firm—Oblon, Spivak, McClelland, Maier & Neustadt, P.C.

(57) ABSTRACT

A method for inspecting a surface of a moving strip to detect surface defects, which includes forming at least one digital picture of at least one face of the strip, in which the digital picture is made up of a set of successive rows of picture elements, each of which is assigned a digital value. The method also includes filtering the at least one digital picture to detect surface irregularities by detecting relative variations in the digital values, and processing the at least one filtered digital picture to identity a type of surface defect corresponding to each detected irregularity. Further, prior to the processing step, an overall characterization of each of the irregularities is performed by determining, a value of predetermined parameters characteristic of surface defects, and a prior classification of the irregularities is performed based on the determined values of the parameters, according to a set of predefined classes. The processing step is performed on each class, and the predetermined parameters characteristic of the surface irregularities is less than a total number of parameters used to identify the defect.

14 Claims, 5 Drawing Sheets

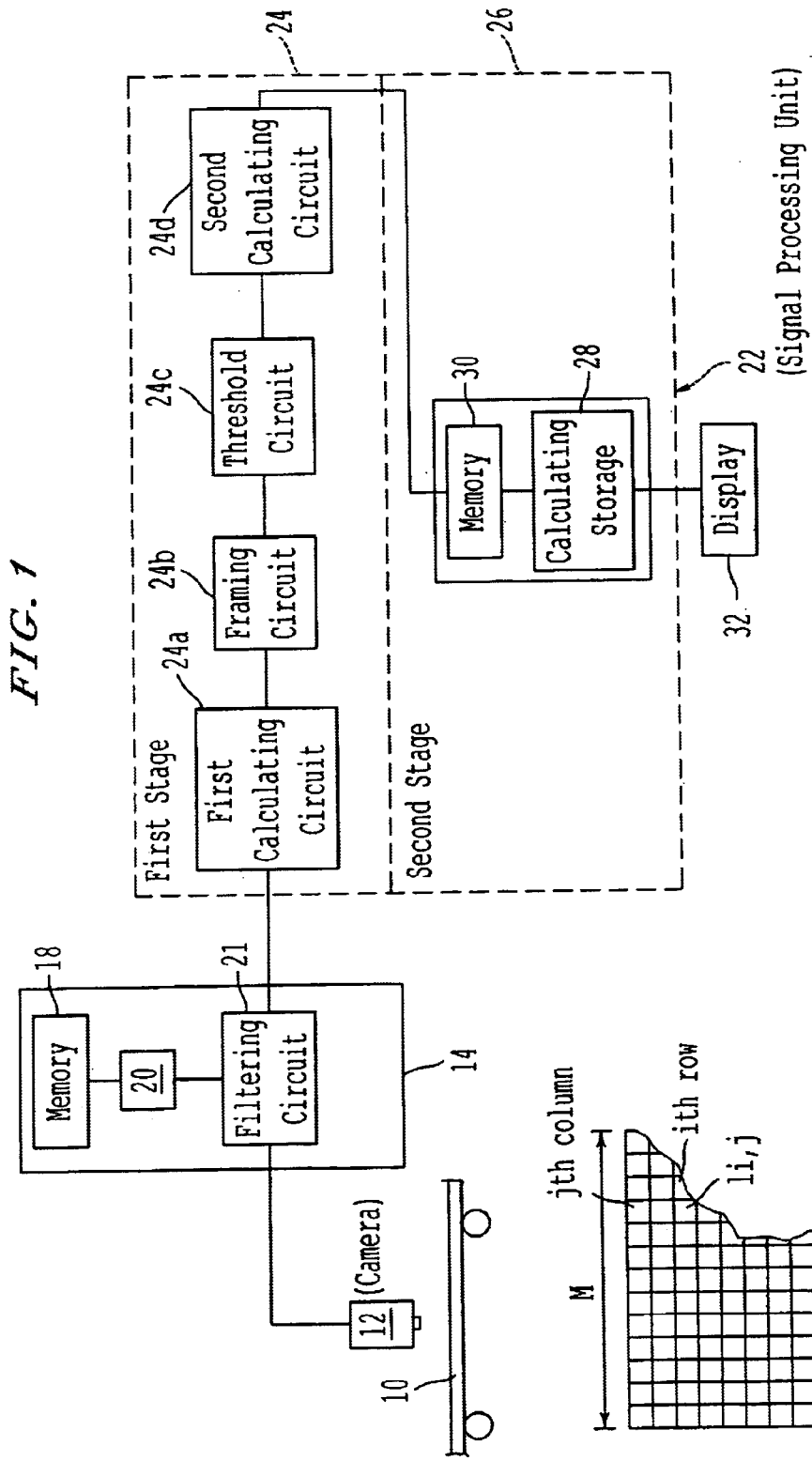

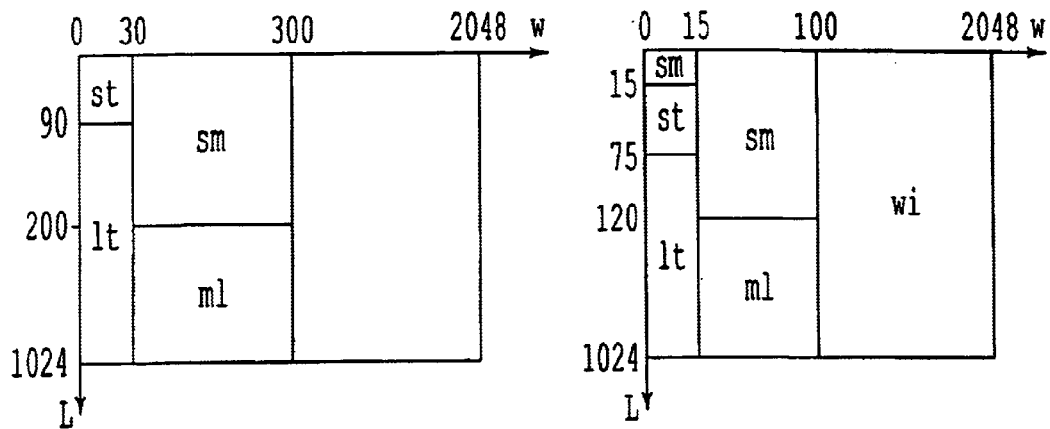
*FIG. 6a*    *FIG. 6b*
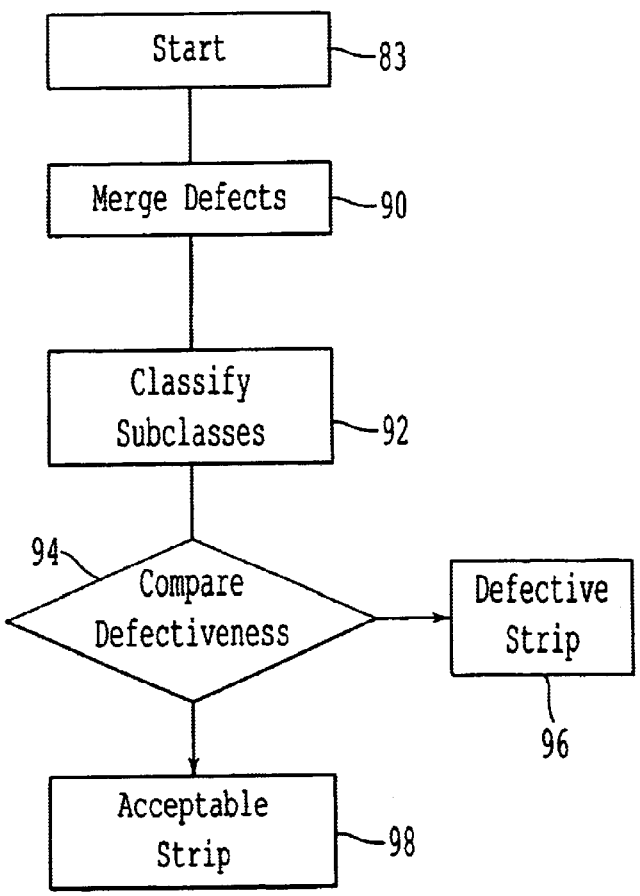
*FIG. 7*

METHOD FOR INSPECTING THE SURFACE OF A MOVING STRIP BY PRIOR CLASSIFICATION OF THE DETECTED SURFACE IRREGULARITY

BACKGROUND OF THE INVENTION

1. Field of the Invention

The present invention relates to a method for inspecting the surface of a moving strip, in particular of rolled sheet metal moving at high speed, for detecting surface defects, as well as to a system employing such an inspection method.

2. Discussion of the Background

In conventional types of surface inspection systems, in which the surfaces of a moving strip are examined automatically, a surface is inspected by forming at least one digital picture of at least one of the faces of the strip, these being made up of a set of successive rows of picture elements which are each assigned a digital value. The at least one digital picture is filtered in order to detect surface irregularities by detecting relative variations in the digital values, and the surface irregularities are processed in order to identify the type of surface defect corresponding to each detected irregularity.

According to this inspection technique, the surface irregularities are generally processed by identifying the defect, from a set of defects liable to occur on the surface being inspected, which corresponds to each irregularity. The analysis of the irregularities is thus carried out in the same way, irrespective of the nature of the detected irregularities.

This type of surface inspection system consequently has relatively low processing speeds, in particular because of the nature of the processing step, which requires a large number of relatively long and complex calculation operations.

SUMMARY OF THE INVENTION

The object of the invention is to overcome these drawbacks and to provide a surface inspection method which allows prior sorting of the detected surface irregularities to be carried out, irrespective of the nature of the surface being inspected.

It therefore relates to a method for inspecting the surface of a moving strip, of the aforementioned type, comprising the steps consisting in:

using photographic means to form at least one digital picture of at least one of the faces of the strip, the digital picture being made up of a set of successive rows of picture elements, each of which is assigned a digital value;

filtering the said at least one digital picture in order to detect surface irregularities by detecting relative variations in the said digital values; and processing the said at least one filtered digital picture in order to identify the type of surface defect corresponding to each detected irregularity;

characterized in that, prior to the step of processing the said at least one digital picture, an overall characterization of the irregularities is carried out by determining, for each of them, the value of predetermined parameters characteristic of surface defects, and a prior classification of the said irregularities is carried out on the basis of the determined values of the said parameters, according to a set of predefined classes, the said processing step being carried out on each class.

Since the detected irregularities are classed beforehand according to a set of classes, on each of which the image processing is carried out, it can be seen that the latter is speeded up considerably with the aid of this prior trimming step.

Further, this prior classification makes it possible to reduce the incidence of recognition errors and therefore improve the quality of the identification.

The method according to the invention may furthermore have one or more of the following characteristics:

each predetermined parameter representing a general reference axis in a space whose dimensions correspond to the said parameters, regions which each correspond to one of the said predefined classes are delimited in the said space, prior to the said prior classification, each irregularity is represented in the said space by a point whose coordinates are the values of the said parameters, and the said prior classification is carried out by identifying the region to which each point belongs, and by assigning the corresponding irregularity to the class corresponding to the said region;

a second way of characterizing the irregularities is determined for each predefined class whose number of characteristic parameters is less than the number of characteristic parameters for overall characterization, and subsequent to the prior classification step, the value of the characteristic parameters of the second characterization method specific to the said class to which the irregularity belongs is determined for each detected irregularity, on the basis of the values of the characteristic parameters for overall characterization;

a simplified reference frame for representing the irregularities is determined for each region, the number of axes of which is less than the number of general reference axes, and subsequent to the prior classification step, a step of changing reference frame from the said general reference to the said simplified reference frame specific to the region to which the irregularity belongs is carried out for each irregularity represented;

the step of processing the irregularities includes a first step of identifying the defect corresponding to each irregularity, from a set of types of defects specific to the class to which the said irregularity belongs, and a second step of classifying the said identified defect with a view to confirming and refining the classification resulting from the said first classification step;

the method includes a step of qualifying the types of defects identified in terms of a first type of defects identified certainly and/or precisely and a second type of defects identified uncertainly and/or imprecisely, and in that the said second classification step is carried out only on the defects of type qualified as uncertain and/or imprecise;

the method further includes a step of grouping together identified defects using a set of predefined criteria, in particular geometric and/or topographical criteria;

the method furthermore includes the steps of counting the number of identified defects of the same type per unit length, and of comparing the said number of defects of each type with a predetermined threshold value representative of the minimum number of defects on the basis of which the said defects are liable to exhibit a periodic character, with a view to detecting periodic defects;

subsequent to the step of determining the value of the said parameters, and before the said prior classification step, a specific classification of the irregularities is carried out according to a set of elementary classes, and the population of the said elementary classes is analysed with a view to detecting periodic defects;

subsequent to the filtering step, in response to detection of a picture element of an irregularity, a storage zone for picture element rows which are successively delivered by the photographic means and include at least one picture element corresponding to at least one irregularity is defined in a memory, each storage zone is segmented into suspect zones each having at least one surface irregularity, suspect zones which are contained in successive storage zones and correspond to the same irregularity are paired, and the total number of rows of picture elements of the paired suspect zones is compared with a threshold for large-length defect detection, and if the said threshold is exceeded, the said step of processing the said at least one filtered digital picture is carried out only on one of the said paired suspect zones, the result of the processing being assigned to the other paired suspect zones.

The invention also relates to a system for inspecting the surface of a moving strip for implementing a method as defined above, characterized in that it has means for photographing at least one of the faces of the strip, a memory for storing at least one picture of the strip in the form of rows and columns of picture elements which are each associated with a digital value, a circuit for filtering the said at least one digital picture in order to detect surface irregularities on the strip, by detecting relative variations in the said digital values, and a unit for processing signals which is connected to the said filtering circuit and comprises means for calculating values of characteristic parameters of surface defects, means for classing the detected irregularities according to a set of clauses predefined on the basis of the values of the said parameters and means for identifying each irregularity from a set of types of defects liable to correspond to the said irregularity.

BRIEF DESCRIPTION OF THE DRAWINGS

Other characteristics and advantages will become apparent from the following description, which is given solely by way of example and with reference to the appended drawings, in which:

FIG. 1 is an overall diagram of one embodiment of a surface inspection system according to the invention;

FIG. 2 represents a part of a picture which is delivered by the photographic means of the system in FIG. 1 and is stored in the memory;

FIGS. 6a and 6b are diagrams which, as a function of the length and the width of the surface defects, show the various classes of defects, respectively for a semi-finished product (DKP) and for a galvanized product; and FIG. 7 is a flow chart showing the steps in a programme for analyzing detected surface defects.

Figure 3A:
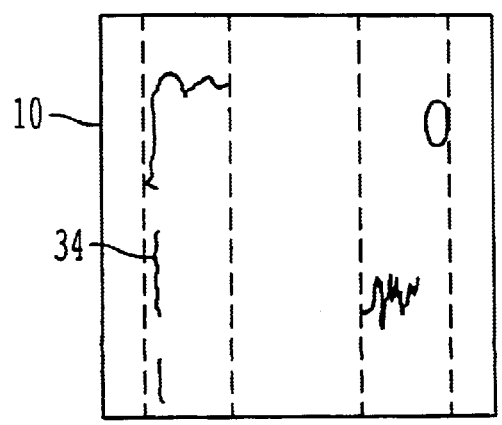
FIGS. 3a to 3e represent various pictures of the surface of a strip during a step of dividing pictures.

DESCRIPTION OF THE PREFERRED EMBODIMENTS.

The system represented in FIG. 1 is intended for detecting surface defects of a strip 10 which is moving at high speed, for example rolled sheet metal leaving a rolling line.

The surfaces of the sheet metal 10 are inspected using a photographic camera 12 which delivers digital pictures of the surface of the strip to a filtering stage 14.

In the illustrative embodiment represented, the system has a single photographic camera 12 aimed at one of the surfaces of the strip, but the system may of course be equipped with two cameras designed to form images of each surface of the strip 10.

The photographic camera 12 may consist of any type of camera suitable for the use in question, whose field width is substantially equal to the width of the inspection zone of the strip 10, which inspection zone may consist of the entire width of the strip. The camera may thus be made up of one or more matrix cameras delivering pictures with finite length, as regards the direction in which the strip is moving, or of one or more linear cameras delivering pictures of infinite length.

If one matrix or linear camera is not sufficient to cover the entire width of the inspection zone of the strip, a plurality of cameras distributed over the width of the strip will be used.

Referring to FIG. 2, the photographic camera 12 forms rows i of M picture elements $I_{i,j}$ or pixels, which can be addressed for identifying the pixels over the length of the strip 10, by the line No. i and, over the width, by column No. j of picture elements, each picture element being associated with a digital value representing a grey level.

The rows of picture elements are stored in a memory 18 of the filtering stage under the direction of a management circuit 20.

According to a first example, the photographic camera consists of a linear camera supplying the memory 18 with 10,000 rows of 2048 pixels per second, these rows being stored in the memory at successive addresses.

According to another example, the photographic camera consists of two matrix cameras which are distributed over the width of the strip in order to cover the width of the strip and are designed to take 10 pictures/s. Each picture delivered by one single camera consists of 1024 rows of 1024 pixels, which are delivered by the memory 18.

The photographic system thus continuously outputs rows of picture elements, each picture element being associated with a digital value representing a grey level. It will be understood that it is synchronized by lines if a linear camera is involved, and synchronized by line groups if a matrix camera is involved.

Referring again to FIG. 1, it can be seen that the filtering stage 14 furthermore has a filtering circuit 21 consisting of an image processing operator which detects relative variations in the digital values of the picture elements, or pixels, in order to detect surface irregularities.

The filtering circuit preferably consists of a contour detection circuit, for example a detector of the "Prewitt" type, which detects variations in grey levels between picture elements lying close to one another, which makes it possible to detect zones of the sheet metal 10 having surface irregularities.

As shown by FIG. 1, the output of the filtering circuit 14 is connected to a signal processing unit 22 which includes a first stage 24 for segmenting the digital pictures into picture element zones which each define a surface irregularity detected by the filtering stage 14, and a second signal processing stage 26, consisting of a calculating circuit 28 associated with a corresponding memory 30 which holds processing algorithms for recognizing and identifying surface defects, for each zone having a surface irregularity.

The system represented in FIG. 1 is furthermore provided with a display device 32 connected to the output of the processing unit 22, one input of which is connected to an output of the calculating circuit 28 and makes it possible to display the detected surface defects associated with information relating to the type of defect and parameters representing the severity of these defects, as will be described in detail below.

The way in which the system which has just been described operates will now be described with reference to FIGS. 2 to 7.

FIG. 3a represents a part of the sheet metal 10 which has a set of surface irregularities such as 34.

Figure 4:
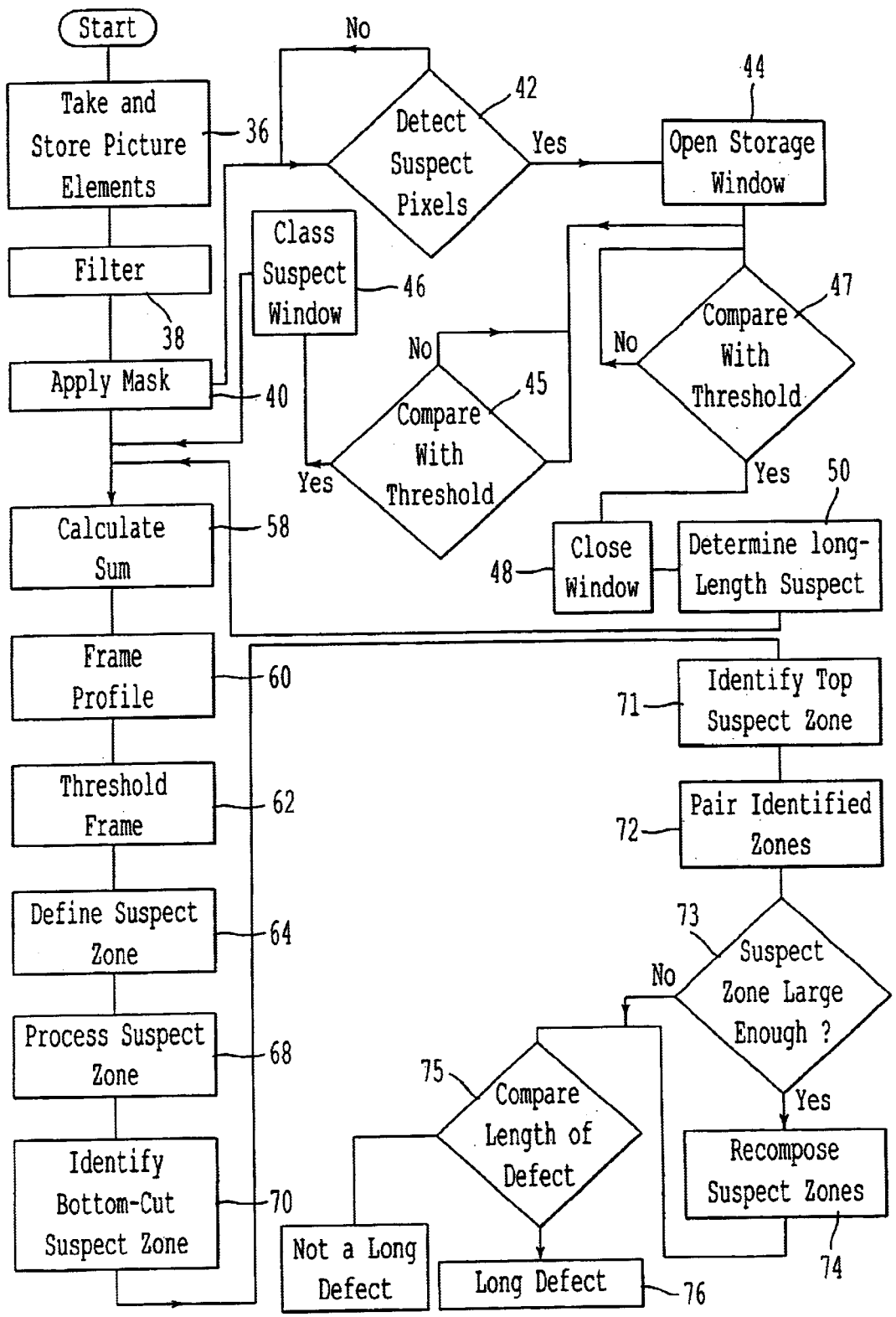
FIG. 4 is a flow chart illustrating the overall way in which the system in FIG. 1 operates.

The field of the photographic camera 12 preferably covers the entire width of the strip 10. Referring to FIG. 4, during a first step 36, the photographic camera takes successive rows of picture elements of the surface of the strip 10, these picture elements being stored, in the memory 18, associated with a grey level value.

During this first photographing step 36, if necessary the management circuit 20 merges the pictures delivered by the photographic camera 12, by grouping together the successive pixels, on the one hand in the direction of the width of the strip 10 in the case when a plurality of cameras are used to cover the full width of the inspection zone, in order to obtain in the memory 18 a picture whose width corresponds to that of the inspected zone, and, on the other hand, in the direction of the length of the strip 10, in the case when the photographic camera 12 uses one or more matrix cameras, by merging the groups of rows of pixels delivered in succession.

The picture stored in the memory 18, referred to below as the "raw picture", is made up of a set of picture elements $I_{i,j}$, i denoting the address of the row in the memory, ranging from 1 to N, and j denoting the number of a picture element of each row and varying from 1 to M, M being equal for example to 2048, each picture element being associated with a grey level digital value.

It should be noted that the value N depends on the capacity of the memory. This capacity should be arranged so as to store a sufficient number of rows, in terms of the subsequent processing to be carried out. For example, in order to store a picture corresponding to a 15 m length of sheet metal with a number of rows of picture elements equal to 1024/m, N is preferably equal to 15,360 rows.

When the capacity of the memory is saturated, rows which arrive successively are stored instead of the oldest rows of pixels stored beforehand and normally processed.

When the memory 18 is saturated and the oldest rows of pixels have not been processed, a saturation alarm is emitted in order to indicate that a zone of the strip will not be inspected.

In this case, the uninspected zone is located on the strip by identifying and storing in a file the successive rows which have not been stored, for example with a view to a statistical analysis of uninspected portions of the strip.

However, in view of the average speed with which the strip moves and the average density of surface irregularities to be identified for a given type of strip, it is possible to determine an average required computing power corresponding to an average processing speed above which there is no longer any risk in practice of erasing unprocessed rows.

The processing modules will therefore preferably be dimensioned so that the instantaneous processing speed is higher than this average speed.

Thus, further to its function of merging the pictures, the memory 18 fulfils a buffer function making it possible to accommodate variations, and in particular increases, in the processing workload owing to an increase in the density of surface irregularities.

During the following step 38, a binary picture representing contour lines of surface irregularities is associated with each picture stored in the memory 18.

To do this, during this step, the successive rows of raw picture elements are filtered by the filtering circuit 21, which as mentioned above consists, for example, of a conventional type of two-way Prewitt filter, having the function of detecting the variations in grey levels of the raw picture elements which signify the existence of surface irregularities, with a view to determining their contour which is written in the associated binary picture.

In the embodiment described, it is assumed that the filter used is a Prewitt filter, but any other type of filter suitable for the use in question may of course also be used.

The Prewitt filter identifies the position of the surface irregularity contour by detecting, on each row of a raw image, picture elements liable to belong to an irregularity contour line, these picture elements being referred to below as "suspect pixels".

The filter which is used here assigns a digital value "1" to each binary picture element associated with each suspect pixel of the raw picture delivered by the photographic camera 12, the other pixels of the binary picture being kept at 0.

This filtering step 38 thus makes it possible to form a binary picture in the memory 18, made up of a set of binary picture elements $B_{i,j}$, to each of which a binary value equal to 1 is assigned for a pixel belonging to a contour of an irregularity, and equal to a zero value for a pixel not belonging to a contour of a surface irregularity.

During the next step 40, the binary picture stored in the memory 18 is processed using a conventional connectivity operator which applies a mask to this picture in order to force to the digital value "1" pixels of the binary picture which have a zero value and lie between two relatively close suspect picture elements, with a view to obtaining and defining continuous lines for each contour detected.

After having undergone this processing, the raw and binary pictures are cleaned to eliminate the spots delimited by a contour whose area is less than a specific threshold, for example 3×3 pixels. This provides a binary picture which is superimposed on the raw picture delivered by the photographic camera 12 and shows the contours defining the surface irregularities detected in the raw picture. The binary picture and the raw picture are then ready for processing.

During the next step 42, the management circuit 20 successively analyzes each row of the stored binary picture in order to detect the binary elements with value "1", that is to say those which are suspect. Once a suspect pixel is detected, the management circuit 20 identifies the number of the corresponding row, opens a storage zone of predetermined capacity in the form of a window in the memory 18 (step 44) starting from this row number, and keeps this window open so long as the management circuit detects suspect pixels in the following rows.

This window, referred to below as the "suspect window", thus contains suspect pixels, that is to say ones liable to belong to a surface irregularity.

The management circuit 20 closes the suspect window again when no suspect pixel has any longer been detected in a predetermined number of successive rows of the binary picture, recording the number of the last row in which a suspect pixel has been identified.

The suspect window thus defined in the memory 18 represents a raw picture segment associated with a corresponding binary picture, and contains at least one surface irregularity which it is desired to identify and recognize.

In particular, the window open during step 44 is kept open so long as the number of the last successive rows of picture elements stored in the window and containing no suspect pixel does not exceed a predetermined threshold number of successive binary rows, this threshold being at least equal to 1.

During the next step 45, the number of successive rows of picture elements not containing any suspect pixel is thus compared with this threshold number and, if they are equal, the suspect window is closed (step 46).

Furthermore, during step 47, the number of rows recorded in the open window is compared with a predetermined threshold termed "long-length window detection" or "detection of a long defect".

This predetermined threshold corresponds to the predetermined maximum capacity of the storage zones in the memory 18.

If the number of rows recorded is higher than this threshold, the window is closed (step 48) and the decision is taken, during the next step 50, that the window is a window termed "long-length suspect", which contains a surface irregularity for which the number of rows of picture elements is higher than the long defect detection threshold.

It will also be noted that, in the embodiment example described, the suspect windows are opened successively.

The surface inspection method continues with phases of dividing the suspect windows stored in the memory 18 into zones which are referred to as "suspect zones" and each have a surface irregularity, using either the component corresponding to the raw picture, or the component corresponding to the binary picture.

To do this, during the next steps 58 to 64, the stage 24 makes a calculation, using suitable means, for example software means, of the accumulation profile of the digital values or the binary values, respectively for each raw picture or each binary picture, on the one hand in the longitudinal direction and, on the other hand, in the width direction, by projecting the digital values or binary values along two perpendicular axes and by thresholding the profiles so as to define suspect regions which each incorporate a surface irregularity.

Although the calculation of this profile can be carried out on the basis of the digital values associated with the picture elements of the raw picture or on the basis of the binary values of the picture stored after processing, in the rest of the description it will be assumed that the processing of the picture is carried out on the basis of the binary picture.

This calculating operation starts with a phase of segmenting each suspect window into a suspect strip encompassing irregularities, each strip then being segmented into one or more suspect zones.

Figure 3B:

Firstly, during step 58, the stage 24 uses a calculating circuit 24-a (FIG. 1) to calculate the sum of the binary values of each row of the suspect window in order to obtain, over M columns, a first transverse profile in the direction of the width of the strip. The curve represented in FIG. 3b is thus obtained.

During the next step 60, this profile is presented to the input of a framing circuit 24-b, in order to be framed so as not to separate picture elements of an irregularity which lie close to one another.

The framing circuit 24-b may consist of any type of suitable filter, such as a finite-impulse response filter FIR, or infinite impulse response filter IIR, but preferably consists of a filter of the moving-window type, making it possible to deliver a framed profile r(x) whose values are determined according to the following equation:

$$r(x) = \sum_{i=-K}^{K} F(x-i) \times Q(i) \qquad (1)$$

in which K denotes the width of the moving window,
  F(x−i) denotes the value of the column (x−i) of the profile to be framed,
  Q denotes the coefficient of the moving-window filter, for example chosen to be equal to 1, and
  x denotes the column number of the framed profile.

The profile framed in this way is then thresholded using a thresholding circuit 24-c, during the next step 62, by comparison with an irregularity-detection threshold value.

Figure 3C:

The framed and thresholded profile represented in FIG. 3c is thus obtained, defining suspect strips which are represented using dashes in FIG. 3a and each encompass one or more surface irregularities.

As mentioned above, the suspect strips defined in this way are then segmented into suspect strips which each have a surface irregularity.

Figure 3D:
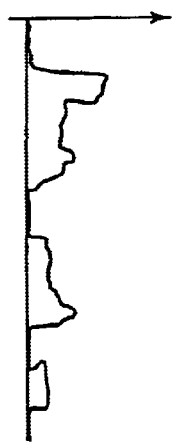

To do this, during the next step 64, steps 58, 60 and 62 are carried out again and applied independently to each row of picture elements of each suspect strip, so as to obtain an accumulation profile of the binary values in the longitudinal direction, as represented in FIG. 3d.

Figure 3E:
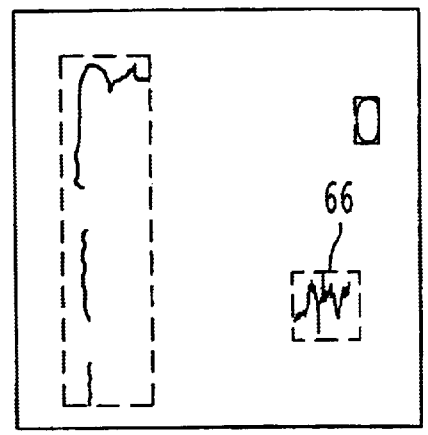

This longitudinal profile is then framed and thresholded, as before, in order to obtain the picture represented in FIG. 3e, in which suspect zones such as 66 are defined, which each delimit a detected surface irregularity, it being of course possible for each irregularity to include a plurality of irregularity segments or objects.

Each suspect zone thus defined therefore contains a raw picture segment and the corresponding binary picture segment.

The suspect zones 66 thus delimited are preferably furthermore presented to the input of a second calculating circuit 24-d, connected to the output of a thresholding circuit 24-c, by means of which the irregularities with small sizes are eliminated.

To do this, during the next step 68, each suspect zone of the binary picture is processed independently using a conventional labelling algorithm with a view to delimiting objects constituting a surface irregularity, each object being defined by a set of suspect picture elements in contact with one another.

The area of each object is then calculated, as is the average area of the objects belonging to a given suspect zone.

The objects with small sizes are eliminated from the processing. To do this, a decision is made to eliminate those objects whose individual area is less than a predetermined percentage of the calculated average area.

This provides, at the output of the calculating circuit 24-d, suspect zones which each contain an irregularity and from which the small objects have been eliminated.

Figure 5:
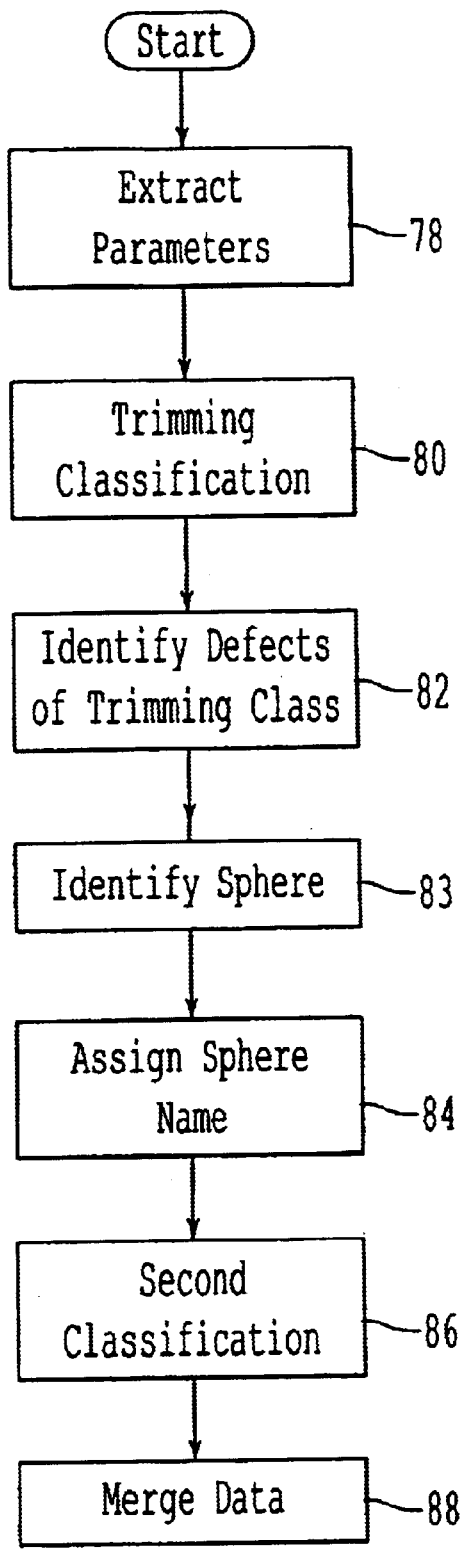
FIG. 5 is a flow chart showing the various steps of processing the filtered digital images.

These suspect zones cleaned in this way are then stored in the memory 30 of the calculating circuit 28 with a view to being processed, as will be described in detail below with reference to FIG. 5.

It should be noted that the calculating 24-a, framing 24-b, and thresholding 24-c and calculating 24-d circuits are circuits of a conventional type. They will not therefore be described in detail below.

In the case when a suspect window has been qualified as a suspect window of large length during the previous step 50, the step of processing the pictures is preceded by a phase of eliminating certain suspect zones from the processing, which makes it possible to reduce the workload of the calculating circuit 28.

To do this, as soon as a suspect window of large length is detected (steps 47, 48 and 50) and cut into suspect zones as described above, during the next step 70 at least one suspect zone of this window whose lower row of picture elements belongs to that of the window is identified. This suspect zone identified in this way is then qualified as a "bottom-cut suspect zone".

The suspect window following a suspect window of large length is qualified as an "extension suspect window".

It will be understood that an extension suspect window may also be of large length.

After cutting, as described above, an extension suspect window in suspect zones, the at least one suspect zone of this window whose upper row of picture elements belongs to that of the window is identified, this suspect zone then being qualified as a "top-cut suspect zone" or "extension suspect zone" (step 71).

The "bottom-cut" suspect zones of the window of large length and the "top-cut" ones of the extension suspect window (step 72) are then paired.

During the next step 73, whether the extension suspect window is itself of large length is determined. If so, at least one suspect zone of this window whose lower row of picture elements belongs to that of the window is identified, this suspect zone then being qualified as before as a "bottom-cut suspect zone", and the same processing is carried out for recomposing this suspect zone with the "top-cut" suspect zones of the next window, termed extension (step 74).

As the pairing or association of the cut suspect zones from one window to the next continues, the length of each defect is updated. During the next step 75, the processing unit 22 compares the length of each defect with the length of a window of large length, that is to say with the long defect detection threshold mentioned above.

As soon as this length exceeds that of a window of large length, the defect is qualified as being a long defect (step 76) and a "long defect group" is opened, which is defined by a zone of the memory of the processing stage in which all the successive cut and associated suspect zones which actually constitute the same defect, referred to as a "long defect", are placed.

All the extension suspect zones which belong to "long defect" groups are then eliminated from the image processing; thus, in each "long defect" group, the image processing is carried out only on the first suspect zone ("bottom-cut") and, to simplify the processing, the result of this processing is assigned to all the extension suspect zones of the same "long defect" group.

As the matching or association of the cut suspect zones from one window to the next continues, by updating the length of each defect associated with suspect zones which correspond to one another from one window to the next, it can be observed during step 75 that this defect is not a long defect.

The segmentation of such a defect cannot take place over more than two successive windows, otherwise it would be qualified as a long defect.

In this case, a storage zone is opened in the memory 30 in the form of a so-called "recomposition" suspect zone, in which the two cut suspect zones of the same defect are placed, suitably joined and centered, the size of the window being adapted in order to frame the said defect as in the case of the uncut suspect zones (step 77).

The recomposition suspect zones are then processed like all the other suspect zones.

Since the phase of segmenting the raw and binary pictures in suspect zones to be processed is now finished, the processing of each suspect zone defined during steps 58 to 68 is then carried out with the exception of the "long defect" group extension suspect zones.

The processing of each suspect zone will now be described with reference to FIGS. 5 and 7.

This processing starts with a step 78 of calculating defect identification parameters, generally qualified as a parameter extraction step.

In a manner which is known per se, the nature is determined of the parameters which are liable to characterize the defects or surface irregularities of the strip to be inspected and are necessary for recognizing them and identifying them accurately and reliably.

The method for calculating these parameters is also determined, in particular on the basis of values of picture elements in the raw or binary picture of a suspect zone containing the defect or the surface irregularity.

In a conventional way, these parameters generally include the length, width and area of a surface irregularity in a suspect zone, the average intensity of the grey levels of the raw picture elements within the defect, the standard deviation of these grey levels, etc.

The number of parameters needed for accurate and reliable recognition, referred to below as P, may be very high and as much as, for example, 65.

With the nature and the method for calculation of the parameters of the defects now being defined for a type of strip to be inspected, calculation of the P parameters for each suspect zone is then carried out.

Each suspect zone or irregularity can thus be represented by a point in a P-dimensional space.

This high number P of parameters is a handicap, in view of the time and processing means for recognizing the suspect zones. In order to avoid this handicap, or at least limit it, a trimming step 80 is carried out which makes it possible to simplify considerably the processing of each suspect zone by classing the irregularities according to a set of trimming classes. This trimming step, which constitutes a prior classification of the irregularities, according to a set of predefined classes, makes it possible to divide the overall problem of analysing the irregularities into a set of problems which are simpler to process.

In particular, within each trimming class, a set of elementary classes or families of defects, the number of which is limited, is defined.

In order to make it possible to carry out the trimming step, it is necessary to have provided a prior phase of defining the trimming classes and, where appropriate, their simplified associated identification, generally before the method according to the invention is carried out.

This prior phase is specific to a type of strip to be inspected.

As an example of a prior phase leading to the definition of trimming classes, the following learning procedure is adopted.

A surface inspection, as described above as far as this stage of the method, is carried out on a sufficient number of samples of the same type of strip to lead to a sufficiently large and representative population of suspect zones, in which each irregularity is represented by a point in the P-dimensional space mentioned above.

According to the generally known method of factorial correspondence analysis, the way in which these points are grouped together as clouds in the space is identified.

It is then assumed that each region in the space delimiting a cloud makes it possible to define a defect typology, and the defects in a given cloud therefore have elements in common and will therefore be able to be possibly represented in a simplified reference frame specific to this cloud or to this typology.

In order to define the axes of a simplified reference frame specific to a typology or to a given cloud, the principal axes of inertia of this cloud may be used, the positions and directions of which can be calculated in a manner which is known per se.

All the defects in a given class can thus be represented in the same simplified reference frame in a space whose dimension is less than P, that is to say all the defects in a given class can be characterized by a reduced number of parameters, less than P.

By employing conventional mathematical methods, change-of-frame matrices are established which make it possible to convert from a representation of the defects in the P-dimensional space to a representation of the same defect in a simplified reference frame with reduced dimensions.

In this prior phase intended to prepare the trimming, typologies or "trimming classes" of defects and a simplified reference frame for defect representation, specific to each trimming class, have thus been defined.

In a specific example, these trimming classes may be defined on the basis of the length (L) or the width (w) of the irregularities; referring to FIGS. 6a and 6b, 5 and 6 trimming classes are for example defined, respectively for "DKP" sheet metal and for galvanized sheet metal, namely a small defect class (sm), a short thin defect class (st), a long thin defect class (lt), a short and medium defect class (sm), a medium and long defect class (ml) and a wide defect class (wi); a simplified representation reference frame being associated with each class.

After the parameter extraction step, the prior classification or trimming step 80 proper can now be implemented.

To do this, each defect or surface irregularity of a suspect zone is distributed into the various trimming classes defined above, on the basis of the value of the P parameters of a defect and the characteristics which define these classes.

This prior distribution of the defects into trimming classes allows the defect recognition to be simplified considerably by carrying out this recognition on each trimming class.

As a variant, all the defects of a given class are represented in the simplified reference frame associated with this class, by using the change-of-frame matrix for this class, applied to the P parameters. This then leads to a simplified characterization of all the defects, using a reduced number of parameters, which limits the amount of calculations to be carried out during recognition.

The subsequent step 82 of the processing consists in recognizing and identifying the defects of each trimming class.

The identification and recognition processing is specific to each trimming class and is generally defined beforehand on the basis of the types of defect which are liable to be encountered in each class.

This identification and recognition processing may consist in a classification based, for example, on the method known as "Coulomb spheres".

Other known methods may also be used, such as the discriminant analysis method, the decision tree method or the method which involves determining the nearest neighbouring "K".

According to the Coulomb spheres method, the defect typologies specific to a given trimming class are represented by spheres, identifiable by position and size, in the simplified space associated with this class.

Each sphere corresponds to a type of defect and/or to a defect identification name.

Thus, in order to recognize and identify a defect of a given trimming class, during step 83 the sphere to which the defect belongs is identified and the identification name associated with this sphere is assigned (step 84).

This recognition and identification operation may advantageously be carried out very rapidly because, since the number of spheres and the number of parameters are reduced because of the previous trimming step, the classification calculations can be carried out on a reduced number of criteria.

In the particular case when, within a given trimming class, a defect not belonging to any sphere is encountered, it is assigned the identification name of the closest sphere.

Thus, at the end of the step 84 of assignation of a defect identification name to each irregularity, all the irregularities are identified as corresponding to a particular type of defect.

The next step 86 consists in carrying out a second classification using a second classification stage of the calculating circuit 28, on the basis of a reduced number of classes in order, for example, to confirm the result given by the first classification stage and to resolve certain ambiguities which may have been found in the identification of certain defects, or in order, for example, to differentiate in terms of more accurate typology between defects of the same type which it was decided not to differentiate between in the first classification stage, for lack of sufficient classification performance at this level.

In order to make it possible to implement this second classification step 86, it is necessary to have provided a prior phase of qualifying each elementary class.

In this prior phase, statistical processing operations are carried out to validate or invalidate the classification carried out for identifying the defects, using the method which has just been described, so as to identify the elementary classes which contain the most defect classification errors.

These elementary classes, of which there is a reduced number, which contain the largest number of classing errors, are qualified as "elementary classes of uncertain identification", and the others, which contain the fewest classing errors, are qualified as "elementary classes of certain identification".

The second classification, implemented in step 86, is carried out only on the defects or irregularities classed in the elementary classes of uncertain identification.

The second classification stage uses, for example, one of the classification methods mentioned above.

It is suitable, for example, for validating or invalidating the membership, of defects, of these classes of uncertain identification. In the case of invalidation, the defect is then considered as not being a defect and is eliminated from the processing.

It may also be suitable, for example, for distributing the defects of certain elementary classes of uncertain identification into classes of precise identification, which are predefined using a more accurate typology.

It should be noted that this additional classification is carried out on a very much reduced number of defect classes and can therefore be performed very rapidly.

Following the steps 80 to 86, each defect is identified and recognized, that is to say assigned to an elementary class.

The image processing phase is concluded with a step 88 of merging the data, during which certain defects are grouped together using criteria defined beforehand, relating in particular to the geometry and the topology of the defects (for example: distance of the defects from one another, identical position above and below the strip, proximity to the edge of the strip, etc.).

This merging phase makes it possible to remedy certain inaccuracies which may occur during the recognition of the defects and solve some particular problems of confusion, without casting doubt on the results which have already been confirmed.

The decision to group the defects together is made after addressing information arising from the close proximity of an object to be recognized, of the order of a metre for example, of other photographic cameras, (for example aimed at the other face of the strip), or data relating to the processing of the strip (nature of the strip, end point, etc.).

In particular, it will be decided to group together defects for which an ambiguity about their name remains, as well as defects of the same nature.

Furthermore, the defects which have particular proximity relationships will be grouped together, that is to say for example the defects located close together, on the same face of the strip or on an opposite face, as well as the defects lying in the same longitudinal or transverse alignment.

For example, in the case of galvanized sheet metal, a defect of the "grain streak" type involves a multitude of surface irregularities lying in the vicinity of the side edge of the sheet metal. In this case, the identification of the defect is not fully reliable. This is because each of these irregularities may be recognized as belonging to a "grain streak", or may be recognized individually as another type of defect, in particular an "exfoliation" or a "blister".

In this particular case, the irregularities which are located in the vicinity of the side edge of the sheet metal and are aligned with one another are merged, and they are identified as belonging to a defect of the "grain streak" type.

Similarly, according to another example, the defects located in the same position, on the upper and lower faces of the sheet metal, are grouped together during this merging step, and they are given the same name.

During this merging step, and as described above with reference to step 76 in FIG. 4, the long defects cut when opening the suspect windows are also grouped together while, as mentioned above, assigning the name of the defect of the suspect zone of large length to the defects of the extension suspect zones of the same group.

During this merging step, the population in each elementary defect class over a given length of strip is also analyzed, that is to say the number of defects per unit length having the same identification.

This population is then compared with a predetermined threshold, referred to as the periodic defect presumption threshold. This threshold is determined for the same given length of strip.

When the population of an elementary class exceeds the said threshold, it is assumed that defects of this class do indeed have a periodic character.

In order to validate this character, a conventional method of detecting periodic defects may be used.

For example, the histogram of the distance between each defect of this class is plotted and, if this histogram demonstrates periodicity (fundamental or harmonic), a specific "periodic defect" group is opened in the memory and the periodic defects of this class are grouped together in this same group.

According to a variant, this step of detecting and grouping together the periodic defects may be carried out after the extraction of the parameters but before the identification and recognition, or even before the trimming or prior classification.

This variant therefore presupposes a specific classification processing which is relatively cursory since it needs to be based on characterizing the defects according to a high number P of parameters and, in order to detect the periodic defects, the population of the elementary classes defined in this specific classification is then analyzed.

This variant has the advantage of displaying a result which does not depend on the performance of the recognition modules (trimming and upstream classification).

After having detected, recognized and possibly grouped together the defects corresponding to detected irregularities, the subsequent phase in the inspection method consists in analyzing the defects with a view to determining their severity, in order to make it possible to determine how defective the strip is. This phase will now be described with reference to FIG. 7.

Beforehand, before the method is implemented, and for each class or type of defect, on the basis of the various intrinsic repercussions possible for this type of defect, a set of subclasses is defined, each subclass being associated with a possible intrinsic repercussion of this type of defect. Each subclass may optionally be assigned an intrinsic severity coefficient.

It can be seen that, at this stage, each surface irregularity is identified and therefore characterized by characteristic parameters, in particular by a reduced number of parameters.

During the first step 90 of this phase of analyzing the defects, the defects, grouped together in a merged group in the previous step, are assimilated to a single defect referred to as a "merged defect". To do this, for these grouped defects, the parameters characterizing the merged defect are calculated by linear combination of the values of the parameters characterizing each defect or irregularity of the merged group.

On the basis of the values of the parameters characterizing the ungrouped defects and the merged defects, during the next step 92, an additional classification of these defects is carried out according to the set of subclasses specific to each type of defect.

This additional classification may be carried out using the same type of methods as those used during the defect recognition.

This additional classification leads to a result independent of the subsequent uses of the sheet metal.

Following this additional classification, an "intrinsic defectiveness profile" of the strip may be defined by a list giving the population of each "severity" subclass of each type or "elementary class" of defect, this population being normalized per unit length of strip; this profile may for example be represented in the form of histograms of the population of each subclass, which are arranged side by side in a predetermined order (subclass after subclass, class after class).

In parallel, for a given use of the strip, the same formalism (for example: histograms in the same order) may be used to define a "permissible defectiveness profile", namely, for each "severity" subclass of each possible type of defect, a maximum permissible population for this given use (still normalized per unit length of strip).

This "permissible defectiveness profile" is not defined "once and for all" for a given use; it may even vary according, for example, to the change in the specifications of this use.

Next, in step 94, the intrinsic defectiveness profile of the inspected strip is compared with the permissible defectiveness profile for the intended use of the said strip.

Thus, during step 94, if it is found that the intrinsic defectiveness profile of the inspected strip falls (or is contained) within the permissible defectiveness profile for the proposed use of this strip, this strip is considered to be acceptable or validated for this use (step 96).

If this is not the case, this inspected strip is considered as unacceptable or "defective" with regard to this use (step 98).

To avoid having to discard this inspected strip, a search is then made for the use within whose permissible defectiveness profile the intrinsic defectiveness profile of this inspected strip falls (or is contained), and this strip is assigned to this other use.

This can be done because sheet metal having a predetermined number of defects of a given severity and a particular type may be not defective for one use, although it is defective for a different use.

For example, sheet metal having a scratch is defective if it is not rolled during a subsequent processing step, but it is considered as not being defective if it is re-rolled, since the scratches will then be flattened out.

The decisive advantage of this method for evaluating the defectiveness of a strip by measuring an intrinsic defectiveness profile is that this measurement is independent of the subsequent downstream use of the strip, and of the variation pertaining to the criteria which need to be satisfied for this use.

The intrinsic defectiveness profiles of the inspected strips may advantageously be used, on the other hand, to monitor the variation and the possible drifts in manufacturing processes for these strips, for example between manufacturing runs; it is thus, for example, possible to identify possible drifts in the behaviour of the rolling plant upstream.

The intrinsic defectiveness profiles of the inspected strips can also be used to identify drifts affecting the inspection system itself.

One possible simplified variant of the method for analysing defectiveness is to assign to each "severity" subclass of types of defects a coefficient whose value depends on the severity estimated for a given use, and the defectiveness profile of a strip may be defined by the sum of the populations of each subclass multiplied by the corresponding coefficient. To validate this use, a check is then simply made that the result obtained, namely the same sum, does not exceed a predetermined value defined for this use.

Other simplified variants based on the use of coefficients may also be envisaged.

What is claimed is:

1. A method for inspecting a surface of a moving strip to detect surface defects, comprising:

forming at least one digital picture of at least one face of the strip, the digital picture being made up of a set of successive rows of picture elements, each of which is assigned a digital value;

filtering the at least one digital picture to detect surface irregularities by detecting relative variations in the digital values; and processing the at least one filtered digital picture to identify a type of surface defect corresponding to each detected irregularity, wherein, prior to the processing step, an overall characterization of each of the irregularities is performed by determining, a value of predetermined parameters characteristic of surface defects, and a prior classification of the irregularities is performed based on the determined values of the parameters, according to a set of pre-defined classes, the processing step being performed on each class, wherein the processing step is specific for each class, wherein the predetermined parameters characteristic of the surface irregularities is less than a total number of parameters used to identify the defect, wherein, each predetermined parameter representing a general reference axis in a space whose dimensions correspond to the parameters, regions which each correspond to one of the predefined classes are delimited in the space, prior to the prior classification, each irregularity is represented in the space by a point whose coordinates are the values of the parameters, and the prior classification is performed by identifying the region to which each point belongs, and by assigning the corresponding irregularity to the class corresponding to the region, and wherein a simplified reference frame for representing the irregularities is determined for each region, a number of axes of which is less then a number of general reference axis, and subsequent to the prior classification step, changing a reference frame from the general reference to the simplified reference frame specific to the region to which the irregularity belongs for each irregularity represented.

2. The method according to claim 1, wherein the processing step includes identifying the defect corresponding to each irregularity, from a set of types of defects specific to the class to which the irregularity belongs, and classifying the identified defect to confirm and refine the classification resulting from the classification step.

3. The method according to claim 2, further comprising qualifying the types of defects identified in terms of a first type of defects identified certainly and a second type of defects identified uncertainly, wherein classifying the identified defect is performed only on the defects of type qualified as uncertain.

4. The method according to claim 1, further comprising grouping together identified defects using a set of predefined criteria.

5. The method according to claim 1, further comprising counting a number of identified defects of a same type per unit length, and comparing the number of defects of each type with a predetermined threshold value representative of a minimum number of defects based on which of the defects exhibit a periodic character to detect periodic defects.

6. The method according to claim 1, wherein after the determining step, and before the prior classification step, a specific classification of the irregularities is performed according to a set of elementary classes, and a population of elementary classes is analyzed to detect periodic defects.

7. The method according to claim 1, wherein after the filtering step, in response to detection of a picture element of an irregularity, a storage zone for picture element rows successively delivered in the forming step and including at least one picture element corresponding to at least one irregularity is defined in a memory, each storage zone is segmented into suspect zones each having at least one surface irregularity, suspect zones which are contained in successive storage zones and correspond to a same irregularity are paired, and a total number of rows of picture elements of the paired suspect zones is compared with a threshold for large-length defect detection, and if the threshold is exceeded, the processing step is performed only on one of the paired suspect zones, a result of the processing being assigned to the other paired suspect zones.

8. A system for inspecting a surface of a moving strip to detect surface defects, comprising;
　a camera configured to form at least one digital picture of at least one face of the strip, the digital picture being made up of a set of successive rows of picture elements, each of which is assigned a digital value;
　a filtering circuit configured to filter the at least one digital picture to detect surface irregularities by detecting relative variations in the digital values; and
　a signal processing unit configured to process the at least one filtered digital picture to identify a type of surface defect corresponding to each detected irregularity,
　wherein, prior to processing the at least one filtered digital picture, an overall characterization of each of the irregularities is performed via the processing unit by determining, a value of predetermined parameters characteristic of surface defects, and a prior classification of the irregularities is performed based on the determined values of the parameters, according to a set of predefined classes, the processing being performed on each class,
　wherein the processing of the signal processing unit is specific for each class,
　wherein the predetermined parameters characteristic of the surface irregularities is less than a total number of parameters used to identify the defect,
　wherein, each predetermined parameter representing a general reference axis in a space whose dimensions correspond to the parameters, regions which each correspond to one of the predefined classes are delimited in the space, prior to the prior classification, each irregularity is represented in the space by a point whose coordinates are the values of the parameters, and the prior classification is performed by identifying the region to which each point belongs, and by assigning the corresponding irregularity to the class corresponding to the region, and
　wherein the processing unit determines a simplified reference frame for representing the irregularities for each region, a number of axes of which is less than a number of general reference axis and subsequent to the prior classification, changes a reference frame from the general reference to the simplified reference frame specific to the region to which the irregularity belongs for each irregularity represented.

9. The system according to claim 8, wherein the processing unit identifies the defect corresponding to each irregularity, from a set of types of defects specific to the class to which the irregularity belongs, and classifies the identified defect to confirm and refine the classification resulting from the classification.

10. The system according to claim 9, wherein the processing unit qualifies the types of defects identified in terms of a first type of defects identified certainly and a second type of defects identified uncertainly,
　wherein the processing unit classifies the identified defect only on the defects of type qualified as uncertain.

11. The system according to claim 8, wherein the processing unit groups together identified defects using a set of predefined criteria.

12. The system according to claim 8, wherein the processing unit counts a number of identified defects of a same type per unit length, and compares the number of defects of each type with a predetermined threshold value representative of a minimum number of defects based on which of the defects exhibit a periodic character to detect periodic defects.

13. The system according to claim 8, wherein after the processing unit determines the value of predetermined parameters, and before the prior classification of the irregularities, the processing unit performs a specific classification of the irregularities according to a set of elementary classes, and analyzes a population of elementary classes to detect periodic defects.

14. The system according to claim 8, wherein after the filtering circuit filters the at least one digital picture, in response to detection of a picture element of an irregularity, the processing unit defines is a memory, a storage zone for picture element rows successively delivered by the camera forming the at least one digital picture and including at least one picture element corresponding to at least one irregularity, each storage zone is segmented into suspect zones each having at least one surface irregularity, suspect zones which are contained in successive storage zones and correspond to a same irregularity are paired, and a total number of rows of picture elements of the paired suspect zones is compared with a threshold for large-length defect detection, and if the threshold is exceeded, the processing unit processes only one of the paired suspect zones, a result of the processing being assigned to the other paired suspect zones.

* * * * *